ns (1) 3-(3,4-dichlorophenyl)-1,1-dimethylurea of the formula and (2) at least one N-substituted halogenoacetanilide of the general formula

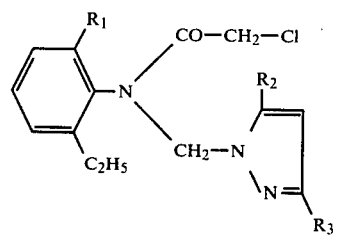

in which
$R^1$ represents methyl or ethyl,
$R^2$ represents hydrogen or methyl and
$R^3$ represents hydrogen or methyl,
are very useful for selectively combating weeds.

13 Claims, No Drawings

United States Patent [19]
Schmidt et al.

[11] 4,294,607
[45] Oct. 13, 1981

[54] HERBICIDAL COMPOSITIONS

[75] Inventors: Robert R. Schmidt, Cologne; Rudolf Thomas, Wuppertal, both of Fed. Rep. of Germany

[73] Assignee: Bayer Aktiengesellschaft, Leverkusen, Fed. Rep. of Germany

[21] Appl. No.: 73,982

[22] Filed: Sep. 10, 1979

[30] Foreign Application Priority Data

Sep. 27, 1978 [DE] Fed. Rep. of Germany ....... 2842003

[51] Int. Cl.³ .................... A01N 43/56; A01N 47/30
[52] U.S. Cl. ........................................... 71/92; 71/120
[58] Field of Search ................................... 71/120, 92

[56] References Cited
U.S. PATENT DOCUMENTS
2,655,447  10/1953  Todd .................................... 71/120

FOREIGN PATENT DOCUMENTS
2648008  5/1978  Fed. Rep. of Germany .

*Primary Examiner*—Catherine L. Mills
*Attorney, Agent, or Firm*—Sprung, Felfe, Horn, Lynch & Kramer

[57] ABSTRACT

Herbicidal compositions containing as active ingredi-

HERBICIDAL COMPOSITIONS

The present invention relates to new herbicidal synergistic combinations of 3-(3,4-dichlorophenyl)-1,1-dimethyl urea and certain N-substituted haloacetanilides.

It is known that 3-(3,4-dichlorophenyl)-1,1-dimethylurea has herbicidal properties (see U.S. Pat. No. 2,655,447). This active compound can thus be employed, for example, for selectively combating weeds in cotton. A disadvantage is, however, that not all the broad-leaved weeds and graminaceous weeds present are always combated.

It is further known that certain N-substituted haloacetanilides for example, 2,6-diethyl-N-(pyrazol-1-yl-methyl)-chloroacetanilide and 2-methyl-6-ethyl-N-(pyrazol-1-yl-methyl)-chloroacetanilide, are suitable as herbicides (see German DE-OS Nos. 2,648,008 and 2,704,281). These substances are mainly active against harmful grasses, such as Avena fatua, Alopecurus, Digitaria, Echinochloa, Panicum, Setaria and others. They can also be employed for selectively combating weeds in, inter alia, cotton. However, for example, in cotton, incompatibility symptoms appear at relatively high dosages.

The present invention now provides a herbicidal composition containing as active ingredients (1) 3-(3,4-dichlorophenyl)-1,1-dimethylurea, of the formula

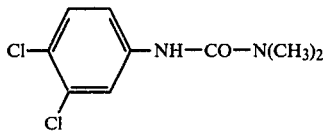

and (2) at least one N-substituted haloacetanilide of the formula

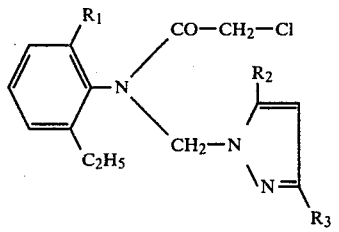

in which
$R^1$ represents methyl or ethyl,
$R^2$ represents hydrogen or methyl and
$R^3$ represents hydrogen or methyl,
alone or in admixture with a diluent or carrier.

The active-compound combinations of this invention have a particularly high selective herbicidal activity.

Surprisingly, the herbicidal activity of the active compound combinations according to the invention is considerably higher than the sum of the actions of the individual active compounds. There is thus a synergistic effect which could not be foreseen, and not just a supplementary action.

It is also particularly surprising that the tolerance by plants of the active compound combinations according to the invention is considerably more favorable than that of the N-substituted haloacetanilides of the formula (II). 3-(3,4-Dichlorophenyl)-1,1-dimethylurea of the formula (I) thus also acts as an "antidote" for the N-substituted haloacetanilides of the formula (II). The active compound combinations according to the invention thus represent a valuable enrichment of the art.

By "antidote" ("safener") in the present connection there is to be understood a substance which is capable of specifically antagonising harmful actions of herbicides on crop plants, that is to say of protecting the crop plants, without reducing the herbicidal action.

The active compounds which the active compound combinations according to the invention contain are already known (see U.S. Pat. No. 2,655,447, DE-OS (German Published Specification) No. 2,648,008 and DE-OS (German Published Specification) No. 2,704,281).

Examples which may be mentioned of active compounds of the formula (II) are: 2,6-diethyl-N-(pyrazol-1-yl-methyl)-chloroacetanilide, 2-methyl-6-ethyl-N-(pyrazol-1-yl-methyl)-chloroacetanilide and 2-methyl-6-ethyl-N-[(3,5-dimethyl-pyrazol-1-yl)-methyl]-chloroacetanilide.

The synergistic effect and the good tolerance by plants of the active compound combinations according to the invention is especially pronounced when the active compounds of the formulae (I) and (II) are present in certain weight ratios. However, the weight ratios of the active compounds can vary in the active compound combinations within relatively wide limits. In general, 0.1 to 10 parts by weight, preferably 0.5 to 5 parts by weight, of active compound of the formula (II) are present per part by weight of active compound of the formula (I).

The active compound combinations according to the invention exhibit a very good action against broad-leaved weeds and graminaceous weeds, for example amongst crops of useful plants. By weeds, in the broadest sense, there are to be understood all plants which grow in locations where they are undesired.

The active compound combinations according to the present invention may be used, for example, to combat the following plants:

dicotyledon weeds of the genera Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Rorippa, Rotala, Lindernia, Lamium, Veronica, Abutilon, Emex, Datura, Viola, Galeopsis, Papaver, Centaurea and Solanum; and monocotyledon weeds of the genera Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monocharia, Fimbristylis, Sagittaria, Eleocharis, Scirpus, Paspalum, Ischaemum, Spenoclea, Dactyloctenium, Agrostis, Alopecurus and Apera.

The active compound combinations according to the present invention may be used, for example, as selective herbicides in the following cultures:

dicotyledon cultures of the genera Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita; and monocotyledon cultures of the genera Oryza, Zea, Triticum, Hordeum, Avena, Secale, Sorghum, Panicum, Saccharum, Ananas, Asparagus and Allium.

However, the use of the active compound combinations according to the invention is in no way restricted to these genera, but also extends in the same manner to other plants.

Use of the active compound combinations according to the invention for selectively combating weeds is preferred in maize, groundnut, beet, soya bean, rice and other varieties of cereal and, in particular, in cotton.

The active compound combinations can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations may be produced in known manner, for example by mixing the active compounds with extenders, that is to say liquid or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compound combinations according to the invention, as such or in the form of their formulations, can also be used, for combating weeds, as mixtures with other herbicides, finished formulations or tank mixing being possible. Mixtures with other active compounds, such as fungicides, insecticides, acaricides, nematicides, bird repellants, growth factors, plant nutrients and agents which improve soil structure, are also possible.

The active compound combinations can be used as such, in the form of their formulations or in the use forms prepared therefrom by further dilution, such as ready-to-use solutions, suspensions, emulsions, powders, pastes and granules. They may be used in the customary manner, for example by watering, spraying, atomising or scattering.

The active compound combinations according to the invention can be applied either before or after emergence of the plants. Application is preferably effected before emergence of the plants, that is to say by the preemergence method. They can also be incorporated into the soil before sowing.

The amount of active compound used can vary within a substantial range. It depends essentially on the nature of the desired effect. In general, the amounts used are from 0.05 to 10 kg of total active compound per hectate, preferably from 0.1 to 5 kg/ha.

The invention therefore also provides a method of combating weeds which comprises applying to the weeds, or to a habitat thereof, a composition according to the present invention.

The invention also provides crops protected from damage by weeds by being grown in areas in which immediately prior to and/or during the time of the growing a composition according to the present invention was applied.

Whereas the individual active compounds exhibit weaknesses in their herbicidal action, the combination shows a broad action against weeds which goes beyond a simple additive action.

A synergistic effect is involved in herbicides whenever the herbicidal action of the active compound combination is greater than that of the individually applied active compounds.

The action to be expected for a given combination of two herbicides can be calculated as follows (see S. R. Colby, "Calculating synergistic and antagonistic responses of herbicide combinations," Weeds 15, pages 20–22, 1967): If X=% damage by herbicide A when using p kg/ha and Y=% damage by herbicide B when using q kg/ha and E=expected damage by herbicides A and B when using p and q kg/ha, then $E = X + Y - (X.Y)/100$ If the actual damage is greater than calculated, the action of the combination is super-additive, that is to say a synergistic effect is concerned.

In the following Example, it is shown that the found herbicidal action of the active-compound combination according to the invention on the weeds is greater than the calculated action, that is to say a genuine synergistic effect is concerned.

EXAMPLE A

Pre-emergence Test

Solvent: 5 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

Seeds of the test plants were sown in normal soil and, after 24 hours, watered with the preparation of the active compound. It was expedient to keep constant the amount of water per unit area. The concentration of the active compound in the preparation was of no importance, only the amount of active compound applied per unit area being decisive. After three weeks, the degree of damage to the plants was determined in % damage in comparison to the development of the untreated control. The figures denoted:
0% = no action (like untreated control)
100% = total destruction The active compounds, the amounts applied and the results can be seen from the table which follows:

It will be understood that the specification and examples are illustrative, but not limitative of the present invention and that other embodiments within the spirit and scope of the invention will suggest themselves to those skilled in the art.

What is claimed is:

1. Herbicidal composition containing a total of 0.1 to 95% by weight as active ingredients
   (1) 3-(3,4-dichlorophenyl)-1,1-dimethylurea, of the formula

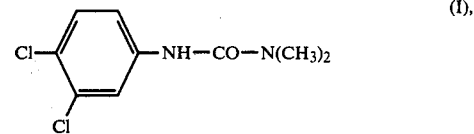

and
(2) at least one N-substituted haloacetanilide compound of the formula

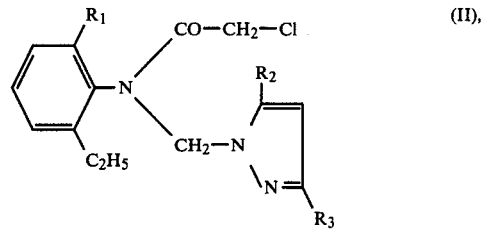

wherein
$R^1$ is methyl or ethyl;
$R^2$ is hydrogen or methyl; and
$R^3$ is hydrogen or methyl.
  in a ratio of between 1:0.5 to 1:5 by weight compound (I):(II).

2. Herbicidal composition as claimed in claim 1 also comprising a diluent or carrier.

3. Herbicidal composition as claimed in claim 1 wherein said compound (II) is 2,6-diethyl-N-(pyrazol-1-yl-methyl)-chloroacetanilide.

4. Herbicidal composition as claimed in claim 1 wherein said compound (II) is 2,6-dimethyl-N-(pyrazol-1-yl-methylchloroacetanilide.

TABLE A

| Active compound or active compound combination | Amount of active compound used kg/ha | Cotton found* | Cotton calculated* | Amaranthus found | Amaranthus calculated | Echinochloa found | Echinochloa calculated |
|---|---|---|---|---|---|---|---|
| (IIa) (known) | 2 | 30 | — | 80 | — | 90 | — |
| (I) (known) | 1 | 0 | — | 70 | — | 10 | — |
| (IIa) + (I) (according to the invention) | 2 + 1 | 0 | 30 | 100 | 94 | 100 | 91 |

*found = found damage
*calculated = calculated damage, according to the Colby formula given earlier.

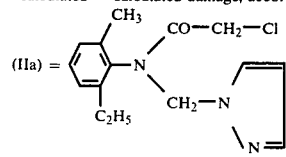

5. Herbicidal composition as claimed in claim 1 wherein said compound (II) is 2-methyl-6-ethyl-N-[(3,5-dimethyl-pyrazol-1-yl)-methyl])-chloroacetanilide.

6. Herbicidal composition as claimed in claim 1 wherein said compound (II) is 2,6-diethyl-N-[(3,5-dimethyl-pyrazol-1-yl)-methyl])-chloroacetanilide.

7. The herbicidal composition of claim 1 comprising two parts compound II to one part compound I by weight.

8. Method of combating broad-leaved or graminaceous weeds growing in an area of corn cultivation comprising applying to the weeds or their habitat, a herbicidal composition as claimed in claim 1.

9. Method of combating broad-leaved or graminaceous weeds growing in an area of groundnut cultivation comprising applying to the weeds or their habitat, a herbicidal composition as claimed in claim 1.

10. Method of combating broad-leaved or graminaceous weeds growing in an area of beet cultivation comprising applying to the weeds or their habitat, a herbicidal composition as claimed in claim 1.

11. Method of combating broad-leaved or graminaceous weeds growing in an area of soya bean cultivation comprising applying to the weeds or their habitat, a herbicidal composition as claimed in claim 1.

12. Method of combating broad-leaved or graminaceous weeds growing in an area of rice cultivation comprising applying to the weeds or their habitat, a herbicidal composition as claimed in claim 1.

13. Method of combating broad-leaved or graminaceous weeds growing in an area of cotton cultivation comprising applying to the weeds or their habitat, a herbicidal composition as claimed in claim 1.

* * * * *